United States Patent [19]
Mito

[11] Patent Number: 6,022,829
[45] Date of Patent: Feb. 8, 2000

[54] HERBICIDAL COMPOSITION

[75] Inventor: Nobuaki Mito, Kobe, Japan

[73] Assignee: Sumitomo Chemical Company, Limited, Osaka-fu, Japan

[21] Appl. No.: 09/147,958

[22] PCT Filed: Feb. 13, 1998

[86] PCT No.: PCT/JP98/00575

§ 371 Date: Mar. 24, 1999

§ 102(e) Date: Mar. 24, 1999

[87] PCT Pub. No.: WO98/35555

PCT Pub. Date: Aug. 20, 1998

[30] Foreign Application Priority Data

Feb. 17, 1997 [JP] Japan ................................. 9-032394
Feb. 17, 1997 [JP] Japan ................................. 9-032396
Feb. 17, 1997 [JP] Japan ................................. 9-032402
Feb. 17, 1997 [JP] Japan ................................. 9-032404

[51] Int. Cl.[7] .................. A01N 43/58; A01N 37/10; A01N 37/34; A01N 43/40; A01N 43/70
[52] U.S. Cl. ............................. 504/134; 504/137
[58] Field of Search ..................... 504/134, 137

[56] References Cited

FOREIGN PATENT DOCUMENTS

WO 96/39392 12/1996 WIPO .
97/07104 2/1997 WIPO ............... A01N 43/58

*Primary Examiner*—S. Mark Clardy
*Attorney, Agent, or Firm*—Sughrue, Mion, Zinn, Macpeak & Seas, PLLC

[57] ABSTRACT

A herbicidal composition for foliar treatment is described, which contains as active ingredients, (a) a compound of general formula [1] wherein R is alkyl, cycloalkyl, alkenyl, dimethylamino, or diethylamino; and (b) a compound selected from the group consisting of atrazine, dicamba, clopyralid, 2,4-D, and bromoxynil. The herbicidal composition is useful for effective control of a wide variety of weeds in upland fields, particularly in corn fields. Also described are a weeding method by foliar treatment of weeds with the above herbicidal composition; and use as a herbicide for foliar treatment, of a mixture of the above active ingredients.

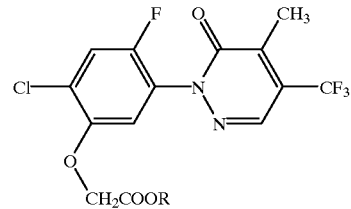

[1]

56 Claims, No Drawings

HERBICIDAL COMPOSITION

This application has been filed under 35 USC 371 as the national stage of international application PCT/JP98/00575, filed Feb. 13, 1998.

TECHNICAL FIELD

The present invention relates to a herbicidal composition, and more particularly, it relates to a herbicidal composition for foliar treatment and a weeding method by foliar treatment of weeds therewith.

BACKGROUND ART

At the present time, numerous herbicides are commercially available and they are widely used. There are, however, many species of weeds to be controlled and their growth extends over a long time. For this reason, requested are herbicides with higher herbicidal activity, wide herbicidal spectrum, and safety to crops.

DISCLOSURE OF INVENTION

The present inventor has intensively studied to find out excellent herbicides. As a result, he has found that various weeds growing in crop lands or non-crop lands can be effectively controlled by foliar treatment of these weeds with a herbicidal composition containing as active ingredients, (a) a compound of the general formula:

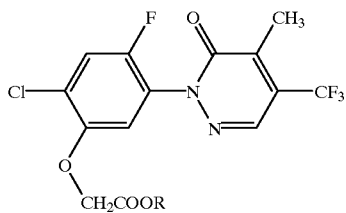

[1]

wherein R is $C_1$–$C_7$ alkyl, $C_5$–$C_6$ cycloalkyl, $C_2$–$C_6$ alkenyl, dimethylamino, or diethylamino; and (b) a compound selected from the group consisting of 6-chloro-$N^2$-ethyl-$N^4$-isopropyl-1,3,5-triazine-2,4-diamine (common name, atrazine; hereinafter referred to as atrazine), 3,6-dichloro-2-methoxybenzoic acid (common name, dicamba; hereinafter referred to as dicamba), 3,6-dichloropicolinic acid (common name, clopyralid; hereinafter referred to as clopyralid), 2,4-dichlorophenoxyacetic acid (common name, 2,4-D; hereinafter referred to as 2,4-D), and 3,5-dibromo-4-hydroxybenzonitrile (common name, bromoxynil; hereinafter referred to as bromoxynil). He has further found that the herbicidal activity is synergistically increased as compared with the cases where the active ingredients are independently used, and the herbicidal composition can, therefore, be applied at a lower amount; and that the herbicidal spectrum is expanded and a wide variety of weeds can be selectively controlled, particularly in corn fields, thereby completing the present invention.

Thus, the present invention provides a herbicidal composition for foliar treatment comprising as active ingredients, (a) a compound of general formula [1] as depicted above, and (b) a compound selected from the group consisting of atrazine, dicamba, clopyralid, 2,4-D, and bromoxynil (hereinafter referred to as the present composition); and a weeding method by foliar treatment of weeds therewith.

MODE FOR CARRYING OUT THE INVENTION

Compound [1], one of the active ingredients of the present composition, can be produced by the methods as described in the following production examples.

Production Example 1

To a solution of 5.3 g (53.3 mmol) of sodium acetate mixed with about 100 ml of water was added under ice cooling 6.6 g (24.3 mmol) of 1,1-dibromo-3,3,3-trifluoro-acetone, and the mixture was stirred at 70° C. for 20 minutes. The reaction mixture was cooled to room temperature, to which a solution of 5.8 g (21.5 mmol) of 2-fluoro-4-chloro-5-isopropoxyphenylhydrazine dissolved in about 20 ml of diethyl ether was added, and the mixture was stirred at room temperature for 1 hour. The ether layer was separated and then concentrated. About 60 ml of tetrahydrofuran (hereinafter referred to as THF) was added to the residue, to which 8.3 g (23.0 mmol) of (carbethoxyethylidene)triphenylphosphorane was added, and the mixture was heated under reflux for 2 hours. The THF was distilled out under reduced pressure, and the residue was subjected to silica gel column chromatography, which afforded 3.8 g (10.5 mmol) of 2-[2-fluoro-4-chloro-5-isopropoxyphenyl]-4-methyl-5-trifluoromethyl-pyridazin-3-one.

Then, 3.5 g (9.7 mmol) of 2-[2-fluoro-4-chloro-5-isopropoxyphenyl]-4-methyl-5-trifluoromethylpyridazin-3-one was dissolved in about 10 ml of concentrated sulfuric acid under ice cooling, and the solution was warmed to room temperature. After ten minutes, about 100 ml of water was added to the reaction mixture. The deposited crystals were collected by filtration, and then washed twice with 20 ml of water and once with 10 ml of hexane in this order. The crystals thus obtained were recrystallized from isopropanol, which afforded 3.2 g (9.9 mmol) of 2-[2-fluoro-4-chloro-5-hydroxy-phenyl]-4-methyl-5-trifluoromethylpyridazin-3-one.

Then, 3.2 g (9.9 mmol) of 2-[2-fluoro-4-chloro-5-hydroxyphenyl]-4-methyl-5-trifluoromethylpyridazin-3-one was dissolved in about 50 ml of N,N-dimethyl-formamide, to which 0.44 g (11 mmol) of sodium hydride (60 wt % oil dispersion) was added at room temperature. The mixture was left stand at room temperature for 30 minutes and then cooled with ice, to which 1.8 g (11 mmol) of ethyl bromoacetate was added. The mixture was stirred at room temperature for 1 hour, to which diethyl ether and water were added in this order to make an extraction. The organic layer was washed with 10% aqueous hydrochloric acid solution, saturated aqueous sodium hydrogencarbonate solution, and saturated aqueous sodium chloride solution in this order, and then dried over anhydrous magnesium sulfate. The solvent was distilled out under reduced pressure, and the residue was subjected to silica gel column chromatography, which afforded 2.4 g (5.5 mmol) of ethyl 2-chloro-4-fluoro-5-(4-methyl-5-trifluoromethyl-3-pyridazinon-2-yl) phenoxyacetate (compound [1] wherein R is ethyl; hereinafter referred to as compound A), m.p., 102.0° C.

Production Example 2

The same procedure as described in Production Example 1 is repeated, except that the following reaction reagents are substituted for ethyl bromoacetate. Thus, the desired ester derivatives of 2-chloro-4-fluoro-5-(4-methyl-5-trifluoromethyl-3-pyrida-zinon-2-yl)phenoxyacetic acid can be obtained.

TABLE 1

| Reaction reagent* | Ester produced* | Compound symbol | Physical property (m.p.) |
| --- | --- | --- | --- |
| Methyl bromoacetate | Methyl ester | B | 80.4° C. |
| Propyl bromoacetate | Propyl ester | C | 82.9° C. |
| Butyl bromoacetate | Butyl ester | D | 75.6° C. |
| Pentyl chloroacetate | Pentyl ester | E | |
| Hexyl bromoacetate | Hexyl ester | F | |
| Heptyl bromoacetate | Heptyl ester | G | 63.2° C. |
| i-Propyl bromoacetate | i-Propyl ester | H | |
| i-Butyl bromoacetate | i-Butyl ester | I | |
| t-Butyl bromoacetate | t-Butyl ester | J | |
| c-Pentyl bromoacetate | c-Pentyl ester | K | |
| c-Hexyl bromoacetate | c-Hexyl ester | L | |
| Allyl bromoacetate | Allyl ester | M | |
| Vinyl chloroacetate | Vinyl ester | N | |

*: "i-", "t-", and "c-" mean iso-, tertiary-, and cyclo-, respectively.

$^1$H-NMR (250 MHz or 300 MHz, CDCl$_3$, TMS, δ(ppm))

Compound E 0.88 (3H, t, J=7 Hz), 1.2–1.4 (4H, m), 1.55–1.70 (2H, m), 2.43 (3H, J=2 Hz), 4.19 (2H, t, J=7 Hz), 4.68 (2H, s), 6.98 (1H, d, J=7 Hz), 7.33 (1H, d, J=8 Hz), 7.99 (1H, s)

Compound H 1.26 (6H, d, J=6.3 Hz), 2.43 (3H, q, J=2 Hz), 4.65 (2H, s), 5.05–5.18 (1H, m), 6.98 (1H, d, J=7 Hz), 7.33 (1H, d, J=8 Hz), 7.98 (1H, s)

Compound I 0.90 (6H, d, J=6.6 Hz), 1.85–2.03 (1H, m), 2.42 (3H, q, J=1.8 Hz), 3.98 (2H, d, J=6.5 Hz), 4.70 (2H, s), 6.99 (1H, d, J=6.3 Hz), 7.33 (1H, d, J=9.1 Hz), 7,98 (1H, s)

Compound J 1.45–1.53 (9H, m), 2.39–2.45 (3H, m), 4.58–4.60 (2H, m), 6.96–7.00 (1H, m,), 7.30–7.36 (1H, m), 7.96–8.00 (1H, m)

Compound K 1.5–1.9 (8H, m), 2.43 (3H, q, J=2 Hz), 4.65 (2H, s), 5.2–5.4 (1H, m d, J=7Hz),7.33(1H, d, J=8Hz),7.98(1H, s)

Compound M 2.42 (3H, q, J=1.9 Hz), 4.67–4.72 (2H, m), 5.23–5.37 (2H, m), 5.84–5.9 (1H, m), 7.00 (1H, d, J=6.3 Hz), 7.33 (1H, d, J=9.2 Hz), 7.99 (1H, s)

Compound N 2.42 (3H, q, J=1.8 Hz), 4.68–4.71 (1H, m), 4.77 (2H, s), 4.94–5.01 (1H, m), 7.03 (1H, d, J=6.3 Hz), 7.26–7.31 (1H, m), 7.34 (1H, d, J=9.0 Hz), 7.99 (1H, s)

Production Example 3

First, 1.0 g of the above compound A was dissolved in 15 ml of 1,4-dioxane, to which 15 ml of concentrated hydrochloric acid was added. This solution was warmed to 60° C., stirred for 6 hours, and then extracted with ethyl acetate. The organic layer was washed with aqueous sodium hydrogencarbonate solution and saturated aqueous sodium chloride solution in this order, and then dried over anhydrous magnesium sulfate. The solvent was distilled out under reduced pressure. The residue was dissolved in 5 g of thionyl chloride, heated under reflux for 1 hour, and then concentrated under reduced pressure. The residue was dissolved in 20 ml of THF at room temperature, to which 0.65 g of N,N-diethylhydroxylamine was added dropwise, and the mixture was then concentrated under reduced pressure. The residue was subjected to silica gel column chromatography, which afforded 1.1 g of O-[2-chloro-4-fluoro- 5-(4-methyl-5-trifluoromethyl-3-pyridazinon-2-yl)phenoxyacetyl]-N,N-diethylhydroxyl-amine (compound [1] wherein R is diethylamino; hereinafter referred to as compound O).

$^1$H-NMR (250 MHz, CDCl$_3$, TMS, δ(ppm)) 1.10 (6H, t, J=7.1 Hz), 2.42 (3H, q, J=1.9 Hz), 2.94 (4H, q, J=7.1 Hz), 4.74 (2H, s), 7.01 (1H, d, J=6.3 Hz), 7.33 (1H d, J=9.1 Hz), 7.97 (1H, s)

Production Example 4

The same procedure as described in Production Example 3 is repeated, except that N,N-dimethylhydroxylamine is substituted for N,N-diethylhydroxylamine. Thus, O-[2-chloro-4-fluoro-5-(4-methyl-5-trifluoromethyl-3-pyridazinon-2-yl)phenoxyacet-yl]-N,N-dimethylhydroxylamine (compound [1] wherein R is dimethylamino; hereinafter referred to as compound P) can be obtained.

Atrazine, dicamba, clopyralid, 2,4-D, and bromoxynil are compounds as described in Farm Chemicals Handbook, 1995 (published by Meister, Publishing Co., 1995), pages C32, C39, C348, C111, and C61, respectively.

Dicamba, clopyralid, and 2,4-D can also be used in the form of agrochemically acceptable salts, and in the context of this specification, "dicamba", "clopyralid", and "2,4-D" include their salts. The salts may include, for example, alkali metal salts; alkaline earth metal salts; amine salts such as isopropylamine salts, dimethylamine salts, and diglycolamine salts; and ammonium salts.

The present invention provides a herbicidal composition that is effective for control of a wide variety of weeds with crop selectivity and for application to a new cultivation method such as non-tillage cultivation. In particular, the herbicidal composition of the present invention effectively controls the main weeds in corn fields, e.g., dicotyledonous plants such as wild buckwheat (*Polygonum convolvulus*), pale smartweed (*Polygonum lapathifolium*), pennsylvania smartweed (*Polygonum pensylvanicum*), common purslane (*Portulaca oleracea*), common lambsquarters (*Chenopodium album*), redroot pigweed (*Amaranthus retroflexus*), wild mustard (*Sinapis arvensis*), hemp sesbania (*Sesbania exaltata*), sicklepod (*Cassia obtusifolia*), velvetleaf (*Abutilon theophrasti*), prickly sida (*Sida spinosa*), ivyleaf morningglory (*Ipomoea hederacea*), tall morningglory (*Ipomoea purpurea*), entireleaf morningglory (*Ipomoea hederacea* var. *integriuscula*), jimsonweed (*Datura stramonium*), black nightshade (*Solanum nigrum*), common cocklebur (*Xanthium strumarium*), common sunflower (*Helianthus annuus*), field bindweed (*Convolvulus arvensis*), sun spurge (*Euphorbia helioscopia*), devils beggarticks (*Bidens frondosa*), and common ragweed (*Ambrosia artemisiifolia*); and monocotyledonous plants such as barnyardgrass (*Echinochloa crus-galli*), green foxtail (*Setaria viridis*), giant foxtail (*Setaria faberi*), yellow foxtail (*Setaria glauca*), southern crabgrass (*Digitaria ciliaris*), goosegrass (*Eleusine indica*), johnsongrass (*Sorghum halepense*), quackgrass (*Agropyron repens*), and shattercane (*Sorghum bicolor*), while it exhibits no significant phytotoxicity on crops such as corn, and succeeding crops to corn, such as soybean.

In the present composition, the mixing ratio of component (a) to component (b), although it may vary with the species of weeds to be controlled, situation and conditions of application, and other factors, is as follows: The weight ratio of compound [1] to atrazine is usually in the range of 1:5 to 500. The weight ratio of compound [1] to dicamba is usually in the range of 1:2 to 200. The weight ratio of compound [1] to clopyralid, 2,4-D, or bromoxynil is usually in the range of 1:1 to 200.

The present composition may be usually used in the form of formulations such as emulsifiable concentrates, wettable powders, or flowables, which can be prepared by mixing the composition with solid carriers, liquid carriers, or other bulking agents, and if necessary, adding surfactants or other adjuvants to this mixture. In such a formulation, component (a) and component (b) are usually contained at the total amount of 0.5 to 90 wt %, preferably 1 to 80 wt %.

The solid carrier to be used in the formulation may include, for example, the following materials in fine powder or granule form: clays (e.g., kaolinite, diatomaceous earth, synthetic hydrated silicon oxide, Fubasami clay, bentonite, acid clay); talc and other inorganic minerals (e.g., sericite, powdered quartz, powdered sulfur, activated carbon, calcium carbonate); and chemical fertilizers (e.g., ammonium sulfate, ammonium phosphate, ammonium nitrate, ammonium chloride, urea). The liquid carrier may include, for example, water; alcohols (e.g., methanol, ethanol); ketones (e.g., acetone, methyl ethyl ketone, cyclohexanone); aromatic hydrocarbons (e.g., toluene, xylene, ethylbenzene, methylnaphthalene); non-aromatic hydrocarbons (e.g., hexane, cyclohexane, kerosine); esters (e.g., ethyl acetate, butyl acetate); nitriles (e.g., acetonitrile, isobutyronitrile); ethers (e.g., dioxane, diisopropyl ether); acid amides (e.g., dimethylformamide, dimethylacetamide); and halogenated hydrocarbons (e.g., dichloroethane, trichloroethylene).

The surfactant may include, for example, alkylsulfate esters; alkylsulfonate salts; alkylarylsulfonate salts; alkyl aryl ethers and their polyoxyethylene derivatives; polyethylene glycol ethers; polyhydric alcohol esters; and sugar alcohol derivatives.

The other adjuvants may include, for example, adhesive agents and dispersing agents, such as casein, gelatin, polysaccharides (e.g., powdered starch, gum arabic, cellulose derivatives, alginic acid), lignin derivatives, bentonite, and synthetic water-soluble polymers (e.g., polyvinyl alcohol, polyvinyl pyrrolidone, polyacrylic acid); and stabilizers such as PAP (isopropyl acid phosphate), BHT (2,6-di-tert-butyl-4-methylphenol), BHA (2-/3-tert-butyl-4-methyoxyphenol), vegetable oils, mineral oils, fatty acids, and fatty acid esters.

The present composition can also be prepared by making the active ingredients into the respective formulations using the above formulation technique and then mixing these formulations.

The present composition thus formulated may be applied to plants as such, or after diluted with water or other solvents. The present composition may also be used in admixture with other herbicides, in which case the herbicidal activity can be expected to be enhanced. The present composition can also be used together with insecticides, bactericides, fungicides, plant growth regulators, fertilizers, soil conditioners, or other agents.

The application amount of the present composition, although it may vary with the mixing ratio of component (a) to component (b) as the active ingredient compounds, weather conditions, formulation types, application times, application methods, application places, weeds to be controlled, and crops to be protected, is usually in the range of 10 to 2000 g as the total amount of active ingredient compounds per hectare. In the case of emulsifiable concentrates, wettable powders, flowables, or other similar formulations, they are usually applied after diluted in their prescribed amounts with water at a ratio of 100 to 1000 liters per hectare.

The following will describe formulation examples, in which parts are by weight.

Formulation Example 1

Two parts of compound A, B, C, D, E, F, G, H, I, J, K, L, M, N, O, or P, 40 parts of atrazine, 3 parts of calcium lignin sulfonate, 2 parts of sodium laurylsulfate, and 53 parts of synthetic hydrated silicon oxide are well pulverized and mixed to give a wettable powder for each compound.

Formulation Example 2

Five parts of compound A, B, C, D, E, F, G, H, I, J, K, L, M, N, O, or P, 40 parts of atrazine, 3 parts of calcium lignin sulfonate, 2 parts of sodium laurylsulfate, and 50 parts of synthetic hydrated silicon oxide are well pulverized and mixed to give a wettable powder for each compound.

Formulation Example 3

Ten parts of compound A, B, C, D, E, F, G, H, I, J, K, L, M, N, O, or P, 40 parts of atrazine, 3 parts of calcium lignin sulfonate, 2 parts of sodium laurylsulfate, and 45 parts of synthetic hydrated silicon oxide are well pulverized and mixed to give a wettable powder for each compound.

Formulation Example 4

Five parts of compound A, B, C, D, E, F, G, H, I, J, K, L, M, N, O, or P, 40 parts of atrazine, 3 parts of polyoxyethylene sorbitan monooleate, 3 parts of CMC (carboxymethylcellulose), and 49 parts of water are mixed and wet pulverized until the particle size comes to 5 microns or smaller to give a flowable for each compound.

Formulation Example 5

Two parts of compound A, B, C, D, E, F, G, H, I, J, K, L, M, N, O, or P, 40 parts of atrazine, 3 parts of polyoxyethylene sorbitan monooleate, 3 parts of CMC (carboxymethylcellulose), and 52 parts of water are mixed and wet pulverized until the particle size comes to 5 microns or smaller to give a flowable for each compound.

Formulation Example 6

Two parts of compound A, B, C, D, E, F, G, H, I, J, K, L, M, N, O, or P, 50 parts of atrazine, 3 parts of calcium lignin sulfonate, 2 parts of sodium laurylsulfate, and 43 parts of synthetic hydrated silicon oxide are well pulverized and mixed to give a wettable powder for each compound.

Formulation Example 7

Two parts of compound A, B, C, D, E, F, G, H, I, J, K, L, M, N, O, or P, 28 parts of dicamba, 3 parts of calcium lignin sulfonate, 2 parts of sodium laurylsulfate, and 65 parts of synthetic hydrated silicon oxide are well pulverized and mixed to give a wettable powder for each compound.

Formulation Example 8

Five parts of compound A, B, C, D, E, F, G, H, I, J, K, L, M, N, O, or P, 70 parts of dicamba, 3 parts of calcium lignin sulfonate, 2 parts of sodium laurylsulfate, and 20 parts of synthetic hydrated silicon oxide are well pulverized and mixed to give a wettable powder for each compound.

Formulation Example 9

Twenty parts of compound A, B, C, D, E, F, G, H, I, J, K, L, M, N, O, or P, 50 parts of dicamba, 3 parts of calcium lignin sulfonate, 2 parts of sodium laurylsulfate, and 25 parts of synthetic hydrated silicon oxide are well pulverized and mixed to give a wettable powder for each compound.

Formulation Example 10

Twenty-five parts of compound A, B, C, D, E, F, G, H, I, J, K, L, M, N, O, or P, 50 parts of dicamba, 3 parts of calcium lignin sulfonate, 2 parts of sodium laurylsulfate, and 20 parts of synthetic hydrated silicon oxide are well pulverized and mixed to give a wettable powder for each compound.

Formulation Example 11

Two parts of compound A, B, C, D, E, F, G, H, I, J, K, L, M, N, O, or P, 28 parts of dicamba, 3 parts of polyoxyethylene sorbitan monooleate, 3 parts of CMC (carboxymethylcellulose), and 64 parts of water are mixed and wet pulverized until the particle size comes to 5 microns or smaller to give a flowable for each compound.

Formulation Example 12

One part of compound A, B, C, D, E, F, G, H, I, J, K, L, M, N, O, or P, 14 parts of dicamba, 3 parts of polyoxyethylene sorbitan monooleate, 3 parts of CMC (carboxymethylcellulose), and 79 parts of water are mixed and wet pulverized until the particle size comes to 5 microns or smaller to give a flowable for each compound.

Formulation Example 13

One part of compound A, B, C, D, E, F, G, H, I, J, K, L, M, N, O, or P, 30 parts of dicamba, 3 parts of polyoxyethylene sorbitan monooleate, 3 parts of CMC (carboxymethylcellulose), and 64 parts of water are mixed and wet pulverized until the particle size comes to 5 microns or smaller to give a flowable for each compound.

Formulation Example 14

Two parts of compound A, B, C, D, E, F, G, H, I, J, K, L, M, N, O, or P, 28 parts of clopyralid, 3 parts of calcium lignin sulfonate, 2 parts of sodium laurylsulfate, and 65 parts of synthetic hydrated silicon oxide are well pulverized and mixed to give a wettable powder for each compound.

Formulation Example 15

Five parts of compound A, B, C, D, E, F, G, H, I, J, K, L, M, N, O, or P, 70 parts of clopyralid, 3 parts of calcium lignin sulfonate, 2 parts of sodium laurylsulfate, and 20 parts of synthetic hydrated silicon oxide are well pulverized and mixed to give a wettable powder for each compound.

Formulation Example 16

Twenty parts of compound A, B, C, D, E, F, G, H, I, J, K, L, M, N, O, or P, 50 parts of clopyralid or a salt thereof, 3 parts of calcium lignin sulfonate, 2 parts of sodium laurylsulfate, and 25 parts of synthetic hydrated silicon oxide are well pulverized and mixed to give a wettable powder for each compound.

Formulation Example 17

Twenty-five parts of compound A, B, C, D, E, F, G, H, I, J, K, L, M, N, O, or P, 50 parts of clopyralid, 3 parts of calcium lignin sulfonate, 2 parts of sodium laurylsulfate, and 20 parts of synthetic hydrated silicon oxide are well pulverized and mixed to give a wettable powder for each compound.

Formulation Example 18

Two parts of compound A, B, C, D, E, F, G, H, I, J, K, L, M, N, O, or P, 28 parts of clopyralid, 3 parts of polyoxyethylene sorbitan monooleate, 3 parts of CMC (carboxymethylcellulose), and 64 parts of water are mixed and wet pulverized until the particle size comes to 5 microns or smaller to give a flowable for each compound.

Formulation Example 19

One part of compound A, B, C, D, E, F, G, H, I, J, K, L, M, N, O, or P, 14 parts of clopyralid or a salt thereof, 3 parts of polyoxyethylene sorbitan monooleate, 3 parts of CMC (carboxymethylcellulose), and 79 parts of water are mixed and wet pulverized until the particle size comes to 5 microns or smaller to give a flowable for each compound.

Formulation Example 20

One part of compound A, B, C, D, E, F, G, H, I, J, K, L, M, N, O, or P, 30 parts of clopyralid, 3 parts of polyoxyethylene sorbitan monooleate, 3 parts of CMC (carboxymethylcellulose), and 64 parts of water are mixed and wet pulverized until the particle size comes to 5 microns or smaller to give a flowable for each compound.

Formulation Example 21

Two parts of compound A, B, C, D, E, F, G, H, I, J, K, L, M, N, O, or P, 28 parts of 2,4-D, 3 parts of calcium lignin sulfonate, 2 parts of sodium laurylsulfate, and 65 parts of synthetic hydrated silicon oxide are well pulverized and mixed to give a wettable powder for each compound.

Formulation Example 22

Five parts of compound A, B, C, D, E, F, G, H, I, J, K, L, M, N, O, or P, 70 parts of 2,4-D, 3 parts of calcium lignin sulfonate, 2 parts of sodium laurylsulfate, and 20 parts of synthetic hydrated silicon oxide are well pulverized and mixed to give a wettable powder for each compound.

Formulation Example 23

Twenty parts of compound A, B, C, D, E, F, G, H, I, J, K, L, M, N, O, or P, 50 parts of 2,4-D, 3 parts of calcium lignin sulfonate, 2 parts of sodium laurylsulfate, and 25 parts of synthetic hydrated silicon oxide are well pulverized and mixed to give a wettable powder for each compound.

Formulation Example 24

Twenty-five parts of compound A, B, C, D, E, F, G, H, I, J, K, L, M, N, O, or P, 50 parts of 2,4-D, 3 parts of calcium lignin sulfonate, 2 parts of sodium laurylsulfate, and 20 parts of synthetic hydrated silicon oxide are well pulverized and mixed to give a wettable powder for each compound.

Formulation Example 25

Two parts of compound A, B, C, D, E, F, G, H, I, J, K, L, M, N, O, or P, 28 parts of 2,4-D, 3 parts of polyoxyethylene sorbitan monooleate, 3 parts of CMC (carboxymethylcellulose), and 64 parts of water are mixed and wet pulverized until the particle size comes to 5 microns or smaller to give a flowable for each compound.

Formulation Example 26

One part of compound A, B, C, D, E, F, G, H, I, J, K, L, M, N, O, or P, 14 parts of 2,4-D, 3 parts of polyoxyethylene sorbitan monooleate, 3 parts of CMC (carboxymethylcellulose), and 79 parts of water are mixed and wet pulverized until the particle size comes to 5 microns or smaller to give a flowable for each compound.

Formulation Example 27

One part of compound A, B, C, D, E, F, G, H, I, J, K, L, M, N, O, or P, 30 parts of 2,4-D, 3 parts of polyoxyethylene sorbitan monooleate, 3 parts of CMC (carboxymethylcellulose), and 64 parts of water are mixed and wet pulverized until the particle size comes to 5 microns or smaller to give a flowable for each compound.

Formulation Example 28

Two parts of compound A, B, C, D, E, F, G, H, I, J, K, L, M, N, O, or P, 28 parts of bromoxynil, 3 parts of calcium lignin sulfonate, 2 parts of sodium laurylsulfate, and 65 parts of synthetic hydrated silicon oxide are well pulverized and mixed to give a wettable powder for each compound.

Formulation Example 29

Five parts of compound A, B, C, D, E, F, G, H, I, J, K, L, M, N, O, or P, 70 parts of bromoxynil, 3 parts of calcium lignin sulfonate, 2 parts of sodium laurylsulfate, and 20 parts of synthetic hydrated silicon oxide are well pulverized and mixed to give a wettable powder for each compound.

Formulation Example 30

Twenty parts of compound A, B, C, D, E, F, G, H, I, J, K, L, M, N, O, or P, 50 parts of bromoxynil, 3 parts of calcium lignin sulfonate, 2 parts of sodium laurylsulfate, and 25 parts of synthetic hydrated silicon oxide are well pulverized and mixed to give a wettable powder for each compound.

Formulation Example 31

Twenty-five parts of compound A, B, C, D, E, F, G, H, I, J, K, L, M, N, O, or P, 50 parts of bromoxynil, 3 parts of calcium lignin sulfonate, 2 parts of sodium laurylsulfate, and 20 parts of synthetic hydrated silicon oxide are well pulverized and mixed to give a wettable powder for each compound.

Formulation Example 32

Two parts of compound A, B, C, D, E, F, G, H, I, J, K, L, M, N, O, or P, 28 parts of bromoxynil, 3 parts of polyoxyethylene sorbitan monooleate, 3 parts of CMC (carboxymethylcellulose), and 64 parts of water are mixed and wet pulverized until the particle size comes to 5 microns or smaller to give a flowable for each compound.

Formulation Example 33

One part of compound A, B, C, D, E, F, G, H, I, J, K, L, M, N, O, or P, 14 parts of bromoxynil, 3 parts of polyoxyethylene sorbitan monooleate, 3 parts of CMC (carboxymethylcellulose), and 79 parts of water are mixed and wet pulverized until the particle size comes to 5 microns or smaller to give a flowable for each compound.

Formulation Example 34

One part of compound A, B, C, D, E, F, G, H, I, J, K, L, M, N, O, or P, 30 parts of bromoxynil, 3 parts of polyoxyethylene sorbitan monooleate, 3 parts of CMC (carboxymethylcellulose), and 64 parts of water are mixed and wet pulverized until the particle size comes to 5 microns or smaller to give a flowable for each compound.

The following will describe test examples.

Evaluation Criteria

The herbicidal activity is evaluated at 11 levels with indices of 0 to 10, i.e., shown by numeral "0", "1", "2", "3", "4", "5", "6", "7", "8", "9", or "10" wherein "0" means that there was no or little difference in the degree of germination or growth between the treated plants and the untreated plants at the time of examination, and "10" means that the test plants died completely or their germination or growth was completely inhibited. The herbicidal activity is excellent when ranked at "7", "8", "9", or "10", but insufficient when ranked at "6" or lower. The phytotoxicity is shown by "no injury" when no significant phytotoxicity was observed; "low" when low phytotoxicity was observed; "moderate" when moderate phytotoxicity was observed; or "high" when high phytotoxicity was observed.

Test Example 1

Plastic pots each having an area of 26.5×19 cm$^2$ and a depth of 7 cm were filled with upland soil, and then seeded with corn (*Zea mays*), giant foxtail (*Setaria faberi*), and southern crabgrass (*Digitaria ciliais*). These test plants were grown in a greenhouse for 23 days.

An emulsifiable concentrate of compound A, which had been obtained by well mixing 10 parts of compound A, 14 parts of polyoxyethylene styryl phenyl ether, 6 parts of calcium dodecylbenzenesulfonate, 35 parts of xylene, and 35 parts of cyclohexa none, a formulation product of atrazine (trade name, AAt rex; Ciba-Geigy Ltd.), and a mixture of the emulsifiable concentrate of compound A and the formulation product of atrazine were independently diluted in their prescribed amounts with water. Each dilution was uniformly sprayed over the test plants with a small sprayer. The same procedure was repeated for compounds E and O. After the application, the test plants were grown in the greenhouse for 4 days, and the herbicidal activity and safety to corn were then examined. The results are shown in Table 2.

TABLE 2

| | | Herbicidal activity | | |
|---|---|---|---|---|
| Compound | Dosage (g/ha) | southern crabgrass | giant foxtail | Phytotoxicity corn |
| Compound A | 20 | 3 | 4 | no injury |
| Compound E | 20 | 3 | 4 | no injury |
| Compound O | 20 | 3 | 4 | no injury |
| Atrazine | 500 | 3 | 2 | no injury |
| Compound A + atrazine | 20 + 500 | 9 | 9 | no injury |
| Compound E + atrazine | 20 + 500 | 9 | 9 | no injury |
| Compound O + atrazine | 20 + 500 | 9 | 9 | no injury |

Test Example 2

Plastic pots each having an area of 26.5×19 cm$^2$ and a depth of 7 cm were filled with upland soil, and then seeded with corn (*Zea mays*), giant foxtail (*Setaria faberi*), and southern crabgrass (*Digitaria ciliaris*). These test plants were grown in a greenhouse: corn, for 16 days; and giant foxtail and southern crabgrass, for 23 days.

An emulsifiable concentrate of compound E, which had been obtained by well mixing 10 parts of compound E, 14 parts of polyoxyethylene styryl phenyl ether, 6 parts of calcium dodecylbenzenesulfonate, 35 parts of xylene, and 35 parts of cyclohexanone, a formulation product of dicamba (trade name, Clarity; Sandoz, Ltd.), and a mixture of the emulsifiable concentrate of compound E and the formulation product of dicamba were independently diluted in their prescribed amounts with water. Each dilution was uniformly sprayed over the test plants with a small sprayer. The same procedure was repeated for compound O. After the application, the test plants were grown in the greenhouse for 4 days, and the herbicidal activity and safety to corn were then examined. The results are shown in Table 3.

TABLE 3

| Compound | Dosage (g/ha) | Herbicidal activity | | Phytotoxicity corn |
|---|---|---|---|---|
| | | southern crabgrass | giant foxtail | |
| Compound E | 20 | 3 | 4 | no injury |
| Compound O | 20 | 3 | 4 | no injury |
| Dicamba | 200 | 1 | 1 | no injury |
| Compound E + dicamba | 20 + 200 | 8 | 8 | no injury |
| Compound O + dicamba | 20 + 200 | 8 | 8 | no injury |

Test Example 3

A upland field was seeded with corn (Zea mays), and the plant was grown for 19 days.

A flowable of compound A, which had been obtained by mixing 10 parts of compound A, 2 parts of a mixture of polyoxyethylene alkylarylphosphate and polyoxyethylene alkyl aryl ether, and 25 parts of water, pulverizing the mixture by wet grinding method so that the particle size came to 5 microns or smaller, adding 11 parts of a thickening agent (xanthan gum and smectite clay) and an antifreezing agent (propylene glycol) to the pulverized mixture, and further adding water so that the total amount came to 100 parts, a formulation product of dicamba as described above, and a mixture of the flowable of compound A and the formulation product of dicamba were independently diluted in their prescribed amounts with water. Each dilution was uniformly sprayed over the test plants, i.e., corn (Zea mays) and southern crabgrass (Digitaria ciliaris) growing in the field, with a sprayer installed on a tractor. On the 7th day after the application, the herbicidal activity and safety to corn were then examined. The results are shown in Table 4.

TABLE 4

| Compound | Dosage (g/ha) | Herbicidal activity southern crabgrass | Phytotoxicity corn |
|---|---|---|---|
| Compound A | 20 | 5 | no injury |
| Dicamba | 280 | 0 | no injury |
| Compound A + dicamba | 20 + 280 | 9 | no injury |

Test Example 4

Plastic pots each having an area of 26.5×19 cm² and a depth of 7 cm were filled with upland soil, and then seeded with corn (Zea mays), giant foxtail (Setaria faberi), southern crabgrass (Digitaria ciliaris), and barnyardgrass (Echinochloa crusgalli). These test plants were grown in a greenhouse for 23 days.

An emulsifiable concentrate of compound A, which had been obtained by well mixing 10 parts of compound A, 14 parts of polyoxyethylene styryl phenyl ether, 6 parts of calcium dodecylbenzenesulfonate, 35 parts of xylene, and 35 parts of cyclohexanone, a formulation product of clopy- ralid (trade name, Stinger; DowElanco), 2,4-D (trade name, 2,4-D amine salt; Nissan Chemical Industries, Ltd.), bromoxynil (trade name, Buctril; Rhone-Poulenc S.A.), a mixture of the emulsifiable concentrate of compound A and the formulation product of clopyralid, a mixture of the emulsifiable concentrate of compound A and the formulation product of 2,4-D, and a mixture of the emulsifiable concentrate of compound A and the formulation product of bromoxynil were independently diluted in their prescribed amounts with water. Each dilution was uniformly sprayed over the test plants with a small sprayer. After the application, the test plants were grown in the greenhouse for 5 days, and the herbicidal activity and safety to corn were then examined. The results are shown in Table 5.

TABLE 5

| Compound | Dosage (g/ha) | Herbicidal activity | | | Phytotoxicity corn |
|---|---|---|---|---|---|
| | | giant foxtail | southern crabgrass | barnyardgrass | |
| Compound A | 20 | 4 | 4 | 6 | no injury |
| Clopyralid | 250 | 0 | 0 | 0 | no injury |
| 2,4-D | 250 | 0 | 0 | 0 | no injury |
| Bromoxynil | 250 | 2 | 2 | 2 | no injury |
| Compound A + clopyralid | 20 + 250 | 7 | 7 | 8 | no injury |
| Compound A + 2,4-D | 20 + 250 | 7 | 7 | 8 | no injury |
| Compound A + bromoxynil | 20 + 250 | 8 | 8 | 9 | no injury |

Industrial Applicability

A wide variety of weeds in upland fields, particularly in corn fields, can be effectively controlled by the present composition.

I claim:

1. A herbicidal composition for foliar treatment comprising as active ingredients,
   (a) a compound of the general formula:

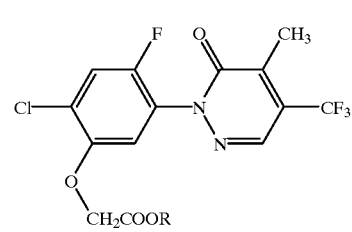

[1]

wherein R is $C_1$–$C_7$ alkyl, $C_5$–$C_6$ cycloalkyl, $C_2$–$C_6$ alkenyl, dimethylamino, or diethylamino; and
   (b) a compound selected from the group consisting of 6-chloro-$N^2$-ethyl-$N^4$-isopropyl-1,3,5-triazine-2,4-diamine (atrazine), 3,6-dichloro-2-methoxybenzoic acid (dicamba), 3,6-dichloropicolinic acid (clopyralid), 2,4-dichlorophenoxyacetic acid (2,4-D), and 3,5-dibromo-4-hydroxybenzonitrile (bromoxynil).

2. The herbicidal composition according to claim 1, for control of weeds in corn fields.

3. The herbicidal composition for foliar treatment according to claim 1, wherein component (a) is compound [1] in which R is $C_1$–$C_7$ alkyl, $C_5$–$C_6$ cycloalkyl, or $C_2$–$C_6$ alkenyl, and component (b) is atrazine.

4. The herbicidal composition for foliar treatment according to claim 3, wherein the weight ratio of component (a) to component (b) is 1:5 to 500.

5. The herbicidal composition according to claim 3 or 4, for control of weeds in corn fields.

6. The herbicidal composition for foliar treatment according to claim 1, wherein component (a) is compound [1] in which R is dimethylamino or diethylamino, and component (b) is atrazine.

7. The herbicidal composition for foliar treatment according to claim 6, wherein the weight ratio of component (a) to component (b) is 1:5 to 500.

8. The herbicidal composition according to claim 6 or 7, for control of weeds in corn fields.

9. The herbicidal composition for foliar treatment according to claim 1, wherein component (a) is compound [1] in which R is $C_1$–$C_7$ alkyl, $C_5$–$C_6$ cycloalkyl, or $C_2$–$C_6$ alkenyl, and component (b) is dicamba.

10. The herbicidal composition for foliar treatment according to claim 9, wherein the weight ratio of component (a) to component (b) is 1:2 to 200.

11. The herbicidal composition according to claim 9 or 10, for control of weeds in corn fields.

12. The herbicidal composition for foliar treatment according to claim 1, wherein component (a) is compound [1] in which R is dimethylamino or diethylamino, and component (b) is dicamba.

13. The herbicidal composition for foliar treatment according to claim 12, wherein the weight ratio of component (a) to component (b) is 1:2 to 200.

14. The herbicidal composition according to claim 12 or 13, for control of weeds in corn fields.

15. The herbicidal composition for foliar treatment according to claim 1, wherein component (b) is a compound selected from the group consisting of clopyralid, 2,4-D, and bromoxynil.

16. The herbicidal composition for foliar treatment according to claim 1, wherein component (a) is compound [1] in which R is $C_1$–$C_7$ alkyl, $C_5$–$C_6$ cycloalkyl, or $C_2$–$C_6$ alkenyl, and component (b) is clopyralid.

17. The herbicidal composition for foliar treatment according to claim 16, wherein the weight ratio of component (a) to component (b) is 1:1 to 200.

18. The herbicidal composition according to claim 16 or 17, for control of weeds in corn fields.

19. The herbicidal composition for foliar treatment according to claim 1, wherein component (a) is compound [1] in which R is $C_1$–$C_7$ alkyl, $C_5$–$C_6$ cycloalkyl, or $C_2$–$C_6$ alkenyl, and component (b) is 2,4-D.

20. The herbicidal composition for foliar treatment according to claim 19, wherein the weight ratio of component (a) to component (b) is 1:1 to 200.

21. The herbicidal composition according to claim 19 or 20, for control of weeds in corn fields.

22. The herbicidal composition for foliar treatment according to claim 1, wherein component (a) is compound [1] in which R is $C_1$–$C_7$ alkyl, $C_5$–$C_6$ cycloalkyl, or $C_2$–$C_6$ alkenyl, and component (b) is bromoxynil.

23. The herbicidal composition for foliar treatment according to claim 22, wherein the weight ratio of component (a) to component (b) is 1:1 to 200.

24. The herbicidal composition according to claim 22 or 23, for control of weeds in corn fields.

25. A weeding method comprising foliar treatment of weeds with a herbicidal composition containing as active ingredients, (a) a compound of the general formula:

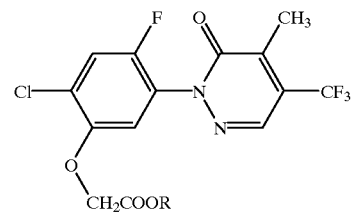

[1]

wherein R is $C_1$–$C_7$ alkyl, $C_5$–$C_6$ cycloalkyl, $C_2$–$C_6$ alkenyl, dimethylamino, or diethylamino; and (b) a compound selected from the group consisting of 6-chloro-$N^2$-ethyl-$N^4$-isopropyl-1,3,5-triazine-2,4-diamine (atrazine), 3,6-dichloro-2-methoxybenzoic acid (dicamba), 3,6-dichloropicolinic acid (clopyralid), 2,4-dichlorophenoxyacetic acid (2,4-D), and 3,5-dibromo-4-hydroxybenzonitrile (bromoxynil).

26. The weeding method according to claim 25, wherein the herbicidal composition is applied to the weeds so that the total amount of component (a) and component (b) is 10 to 2000 g/ha.

27. The weeding method according to claim 25 or 26, wherein the herbicidal composition is applied to the weeds in corn fields.

28. The weeding method according to claim 25 or 26, wherein component (a) is compound [1] in which R is $C_1$–$C_7$ alkyl, $C_5$–$C_6$ cycloalkyl, or $C_2$–$C_6$ alkenyl, and component (b) is atrazine.

29. The weeding method according to claim 28, wherein the weight ratio of component (a) to component (b) is 1:5 to 500.

30. The weeding method according to claim 28, wherein the herbicidal composition is applied to the weeds in corn fields.

31. The weeding method according to claim 25 or 26, wherein component (a) is compound [1] in which R is dimethylamino or diethylamino, and component (b) is atrazine.

32. The weeding method according to claim 31, wherein the weight ratio of component (a) to component (b) is 1:5 to 500.

33. The weeding method according to claim 31, wherein the herbicidal composition is applied to the weeds in corn fields.

34. The weeding method according to claim 25 or 26, wherein component (a) is compound [1] in which R is $C_1$–$C_7$ alkyl, $C_5$–$C_6$ cycloalkyl, or $C_2$–$C_6$ alkenyl, and component (b) is dicamba.

35. The weeding method according to claim 34, wherein the weight ratio of component (a) to component (b) is 1:2 to 200.

36. The weeding method according to claim 34, wherein the herbicidal composition is applied to the weeds in corn fields.

37. The weeding method according to claim 25 or 26, wherein component (a) is compound [1] in which R is dimethylamino or diethylamino, and component (b) is dicamba.

38. The weeding method according to claim 37, wherein the weight ratio of component (a) to component (b) is 1:2 to 200.

39. The weeding method according to claim 37, wherein the herbicidal composition is applied to the weeds in corn fields.

40. The weeding method according to claim 25 or 26, wherein component (b) is one selected from the group consisting of clopyralid, 2,4-D, and bromoxynil.

41. The weeding method according to claim 25 or 26, wherein component (a) is compound [1] in which R is $C_1$–$C_7$ alkyl, $C_5$–$C_6$ cycloalkyl, or $C_2$–$C_6$ alkenyl, and component (b) is clopyralid.

42. The weeding method according to claim 41, wherein the weight ratio of component (a) to component (b) is 1:1 to 200.

43. The weeding method according to claim 41, wherein the herbicidal composition is applied to the weeds in corn fields.

44. The weeding method according to claim 25 or 26, wherein component (a) is compound [1] in which R is $C_1$–$C_7$ alkyl, $C_5$–$C_6$ cycloalkyl, or $C_2$–$C_6$ alkenyl, and component (b) is 2,4-D.

45. The weeding method according to claim 44, wherein the weight ratio of component (a) to component (b) is 1:1 to 200.

46. The weeding method according to claim 44, wherein the herbicidal composition is applied to the weeds in corn fields.

47. The weeding method according to claim 25 or 26, wherein component (a) is compound [1] in which R is $C_1$–$C_7$ alkyl, $C_5$–$C_6$ cycloalkyl, or $C_2$–$C_6$ alkenyl, and component (b) is bromoxynil.

48. The weeding method according to claim 47, wherein the weight ratio of component (a) to component (b) is 1:1 to 200.

49. The weeding method according to claim 47, wherein the herbicidal composition is applied to the weeds in corn fields.

50. The weeding method according to claim 29, wherein the herbicidal composition is applied to the weeds in corn fields.

51. The weeding method according to claim 32, wherein the herbicidal composition is applied to the weeds in corn fields.

52. The weeding method according to claim 35, wherein the herbicidal composition is applied to the weeds in corn fields.

53. The weeding method according to claim 38, wherein the herbicidal composition is applied to the weeds in corn fields.

54. The weeding method according to claim 42, wherein the herbicidal composition is applied to the weeds in corn fields.

55. The weeding method according to claim 45, wherein the herbicidal composition is applied to the weeds in corn fields.

56. The weeding method according to claim 48, wherein the herbicidal composition is applied to the weeds in corn fields.

* * * * *